United States Patent
Kerr (10) Patent No.: US 8,734,444 B2
(45) Date of Patent: May 27, 2014

(54) SYSTEM AND METHOD FOR DELIVERING HIGH CURRENT TO ELECTROSURGICAL DEVICE

(75) Inventor: Duane E. Kerr, Berthoud, CO (US)

(73) Assignee: Covidien LP, Mansfield, MA (US)

( * ) Notice: Subject to any disclaimer, the term of this patent is extended or adjusted under 35 U.S.C. 154(b) by 1072 days.

(21) Appl. No.: 12/249,218

(22) Filed: Oct. 10, 2008

(65) Prior Publication Data

US 2010/0094288 A1 Apr. 15, 2010

(51) Int. Cl.
*A61B 18/18* (2006.01)

(52) U.S. Cl.
USPC ............... 606/51; 606/39; 606/40; 606/48; 606/52

(58) Field of Classification Search
USPC ......... 606/45, 46, 47, 48, 49, 50, 51, 52, 205, 606/206, 207, 208, 209, 210, 211
See application file for complete search history.

(56) References Cited

U.S. PATENT DOCUMENTS

| | | | |
|---|---|---|---|
| 3,478,744 A | 11/1969 | Leiter | |
| 3,513,353 A | 5/1970 | Lansch | |
| 3,595,221 A | 7/1971 | Blackett | |
| 3,611,053 A | 10/1971 | Rowell | |
| 3,641,422 A | 2/1972 | Farnsworth et al. | |
| 3,875,945 A | 4/1975 | Friedman | |
| 4,126,137 A | 11/1978 | Archibald | |
| 4,590,934 A | 5/1986 | Malis et al. | |
| 4,651,264 A | 3/1987 | Shiao-Chung Hu | |
| 4,788,634 A | 11/1988 | Schlecht et al. | |
| 4,887,199 A | 12/1989 | Whittle | |
| 5,244,462 A * | 9/1993 | Delahuerga et al. | 606/42 |
| 5,269,780 A * | 12/1993 | Roos | 606/42 |
| 5,334,193 A * | 8/1994 | Nardella | 606/41 |
| 5,342,357 A | 8/1994 | Nardella | |
| 5,445,635 A * | 8/1995 | Denen et al. | 606/27 |
| 5,472,443 A | 12/1995 | Cordis et al. | |
| 5,694,304 A | 12/1997 | Telefus et al. | |
| 5,696,441 A | 12/1997 | Mak et al. | |
| 5,712,772 A | 1/1998 | Telefus et al. | |
| 5,807,253 A | 9/1998 | Dumoulin et al. | |
| 5,836,943 A | 11/1998 | Miller, III | |
| 6,113,596 A * | 9/2000 | Hooven et al. | 606/42 |
| 6,222,356 B1 | 4/2001 | Taghizadeh-Kaschani | |
| 6,228,081 B1 * | 5/2001 | Goble | 606/34 |
| 6,238,387 B1 | 5/2001 | Miller, III | |

(Continued)

FOREIGN PATENT DOCUMENTS

| | | |
|---|---|---|
| DE | 179607 | 3/1905 |
| DE | 1099658 | 2/1961 |

(Continued)

OTHER PUBLICATIONS

U.S. Appl. No. 12/057,557, filed Mar. 28, 2008.

(Continued)

*Primary Examiner* — Kevin C Sirmons
*Assistant Examiner* — William Carpenter (57) ABSTRACT

An electrosurgical system is disclosed. The system includes an electrosurgical generator adapted to supply electrosurgical power and an electrosurgical device coupled to the electrosurgical generator. The electrosurgical device includes a transformer and one or more active electrodes coupled thereto, wherein the transformer is adapted to step down the voltage of the power supplied by the electrosurgical generator.

6 Claims, 5 Drawing Sheets

(56) References Cited

U.S. PATENT DOCUMENTS

| | | | |
|---|---|---|---|
| 6,398,781 B1* | 6/2002 | Goble et al. | 606/41 |
| 6,428,537 B1 | 8/2002 | Swanson et al. | |
| 6,547,786 B1 | 4/2003 | Goble | |
| 6,740,079 B1 | 5/2004 | Eggers | |
| 6,923,804 B2 | 8/2005 | Eggers et al. | |
| RE39,358 E | 10/2006 | Goble | |
| 7,316,682 B2* | 1/2008 | Konesky | 606/40 |
| 7,344,532 B2 | 3/2008 | Goble et al. | |
| 7,396,336 B2 | 7/2008 | Orszulak et al. | |
| 7,422,582 B2 | 9/2008 | Malackowski et al. | |
| 2003/0181898 A1 | 9/2003 | Bowers | |
| 2004/0030328 A1* | 2/2004 | Eggers et al. | 606/34 |
| 2005/0015085 A1* | 1/2005 | McClurken et al. | 606/45 |
| 2005/0113820 A1* | 5/2005 | Goble et al. | 606/34 |
| 2005/0171533 A1* | 8/2005 | Latterell et al. | 606/48 |
| 2006/0116675 A1* | 6/2006 | McClurken et al. | 606/51 |
| 2008/0082094 A1 | 4/2008 | McPherson et al. | |
| 2008/0132893 A1* | 6/2008 | D'Amelio et al. | 606/52 |
| 2008/0287791 A1 | 11/2008 | Orszulak et al. | |
| 2008/0287838 A1 | 11/2008 | Orszulak et al. | |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4339049 | 5/1995 |
| DE | 19717411 | 11/1998 |
| DE | 19848540 | 5/2000 |
| EP | 246350 | 11/1987 |
| EP | 310431 | 4/1989 |
| EP | 325456 | 7/1989 |
| EP | 390937 | 10/1990 |
| EP | 556705 | 8/1993 |
| EP | 608609 | 8/1994 |
| EP | 836868 | 4/1998 |
| EP | 1051948 | 11/2000 |
| EP | 1053720 | 11/2000 |
| EP | 880220 | 6/2006 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| GB | 607850 | 9/1948 |
| GB | 702510 | 1/1954 |
| GB | 855459 | 11/1960 |
| GB | 902775 | 8/1962 |
| GB | 2164473 | 3/1986 |
| GB | 2214430 | 9/1989 |
| GB | 2358934 | 8/2001 |
| SU | 166452 | 1/1965 |
| SU | 727201 | 4/1980 |
| WO | WO96/02180 | 2/1996 |
| WO | WO98/07378 | 2/1998 |

OTHER PUBLICATIONS

U.S. Appl. No. 10/406,690, filed Apr. 3, 2003.
U.S. Appl. No. 11/242,458, filed Oct. 3, 2005.
U.S. Appl. No. 10/573,713, filed Mar. 28, 2006.
U.S. Appl. No. 12/136,620, filed Jun. 10, 2008.
U.S. Appl. No. 12/389,168, filed Feb. 19, 2009.
U.S. Appl. No. 12/351,935, filed Jan. 12, 2009.
U.S. Appl. No. 12/401,981, filed Mar. 11, 2009.
U.S. Appl. No. 12/351,947, filed Jan. 12, 2009.
U.S. Appl. No. 12/407,896, filed Mar. 20, 2009.
U.S. Appl. No. 12/205,525, filed Sep. 5, 2008.
U.S. Appl. No. 12/249,263, filed Oct. 10, 2008.
U.S. Appl. No. 12/249,218, filed Oct. 10, 2008.
U.S. Appl. No. 12/351,970, filed Jan. 12, 2009.
U.S. Appl. No. 12/351,960, filed Jan. 12, 2009.
U.S. Appl. No. 12/205,298, filed Sep. 5, 2008.
U.S. Appl. No. 12/351,980, filed Jan. 12, 2009.
U.S. Appl. No. 12/203,734, filed Sep. 3, 2008.
U.S. Appl. No. 12/242,102, filed Sep. 30, 2008.
U.S. Appl. No. 12/241,861, filed Sep. 30, 2008.
U.S. Appl. No. 12/242,061, filed Sep. 30, 2008.
U.S. Appl. No. 12/242,026, filed Sep. 30, 2008.
U.S. Appl. No. 12/241,905, filed Sep. 30, 2008.
U.S. Appl. No. 12/241,942, filed Sep. 30, 2008.
U.S. Appl. No. 12/241,983, filed Sep. 30, 2008.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . . " Journal of Applied Sciences-Yingyong Kexue Xuebao, Shangha CNn, vol. 23 No. 2;(Mar. 2005); pp. 160-164.

(56) References Cited

OTHER PUBLICATIONS

Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.

* cited by examiner

SYSTEM AND METHOD FOR DELIVERING HIGH CURRENT TO ELECTROSURGICAL DEVICE

BACKGROUND

1. Technical Field

The present disclosure relates to electrosurgical apparatuses, systems and methods. More particularly, the present disclosure is directed to electrosurgical devices adapted for delivery of high current.

2. Background of Related Art

Electrosurgery involves application of high radio frequency electrical current to a surgical site to cut, seal, ablate, or coagulate tissue. In monopolar electrosurgery, a source or active electrode delivers radio frequency energy from the electrosurgical generator to the tissue and a return electrode carries the current back to the generator. In monopolar electrosurgery, the source electrode is typically part of a surgical instrument held by the surgeon and applied to the tissue to be treated. A patient return electrode is placed remotely from the active electrode to carry the current back to the generator.

In bipolar electrosurgery, a hand-held instrument typically carries two electrodes, e.g., electrosurgical forceps. One of the electrodes of the hand-held instrument functions as the active electrode and the other as the return electrode. The return electrode is placed in close proximity to the active (i.e., current supplying) electrode such that an electrical circuit is formed between the two electrodes. In this manner, the applied electrical current is limited to the body tissue positioned between the two electrodes.

In certain situations it is desirable to operate the electrosurgical instruments using relatively long connection cables. Due to the increase in cable length, the resistance of the wires within the cables limits the current that can be supplied directly to the instruments from the generator.

SUMMARY

According to one embodiment of the present disclosure, an electrosurgical system is provided. The system includes an electrosurgical generator adapted to supply electrosurgical power and an electrosurgical device coupled to the electrosurgical generator. The electrosurgical device includes a transformer and one or more active electrodes coupled thereto, wherein the transformer is adapted to step down the voltage of the power supplied by the electrosurgical generator.

According to another embodiment of the present disclosure, an electrosurgical instrument is provided. The instrument is configured to couple to an electrosurgical generator that is adapted to supply electrosurgical power to the electrosurgical instrument. The electrosurgical instrument includes at least one active electrode and a transformer coupled to the at least one active electrode. The transformer is adapted to step down the voltage of the power supplied by the electrosurgical generator.

A method for transmitting electrosurgical energy is also contemplated by the present disclosure. The method includes the steps of generating electrosurgical power at an electrosurgical generator, transmitting electrosurgical power to an electrosurgical device including a transformer and one or more active electrodes coupled thereto and stepping down the voltage of the electrosurgical power supplied by the electrosurgical generator prior to supplying the stepped down voltage electrosurgical power to the active electrodes.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

The present disclosure relates to electrosurgical instruments that are adapted to receive high frequency electrical energy from an electrosurgical generator. The instruments according to the present disclosure can perform bipolar electrosurgical procedures, including vessel sealing procedures. The generator may include a plurality of outputs for interfacing with various electrosurgical instruments (e.g., bipolar electrosurgical forceps, footswitch, etc.). Further, the generator includes electronic circuitry configured for generating radio frequency power specifically suited for various electrosurgical nodes and procedures (e.g., bipolar, vessel sealing).

Figure 1:
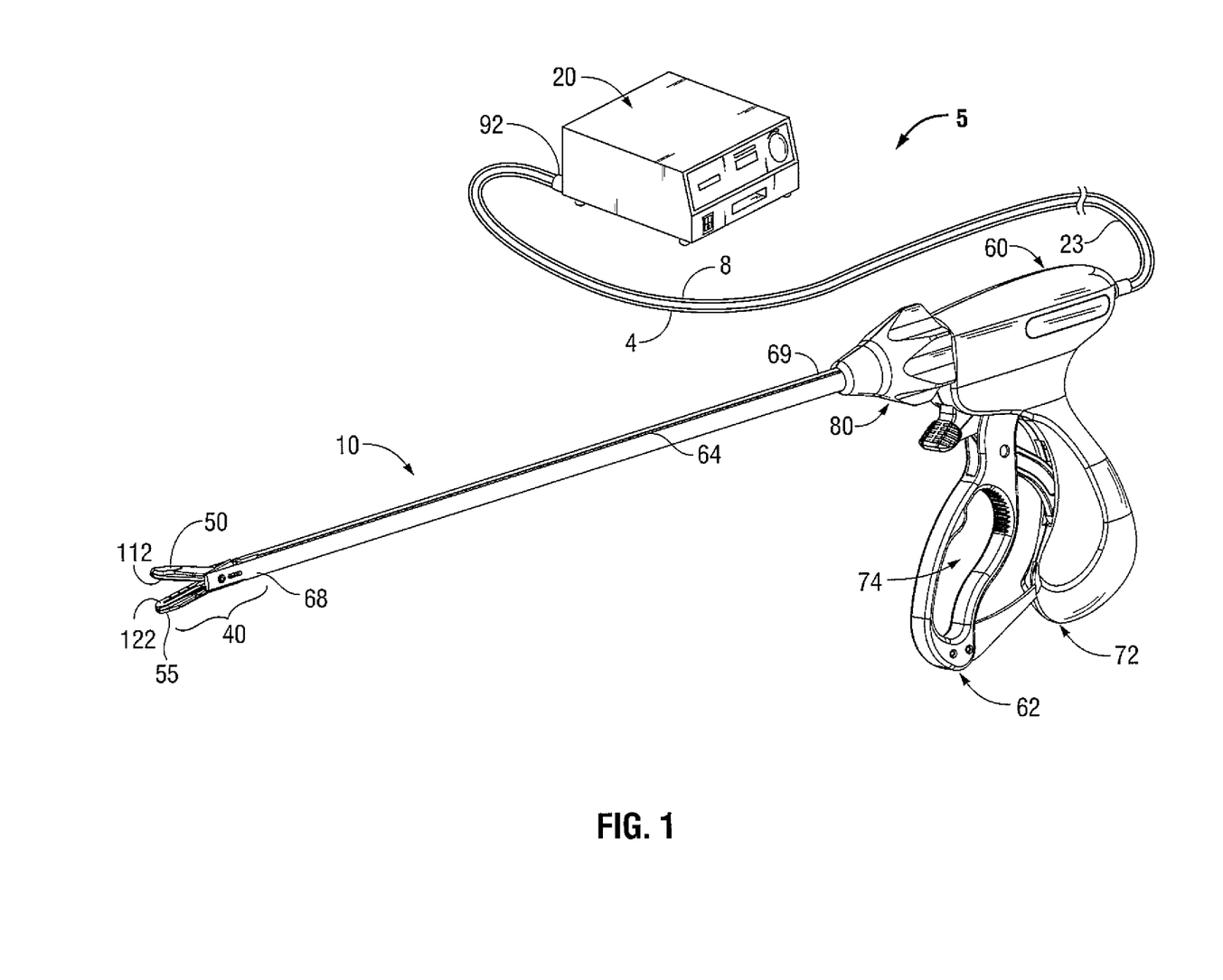
FIG. 1 is a schematic block diagram of a bipolar electrosurgical system in accordance with an embodiment of the present disclosure.

FIG. 1 shows a bipolar electrosurgical system 5 according to the present disclosure that includes an electrosurgical forceps 10 having opposing jaw members 50 and 55. The forceps 10 includes a shaft member 64 having an end effector assembly 40 disposed at the distal end thereof. The end effector assembly 40 includes two jaw members 50 and 55 movable from a first position wherein the jaw members 50 and 55 are spaced relative to another to a closed position wherein the jaw members 50 and 55 cooperate to grasp tissue therebetween. Each of the jaw members 50 and 55 includes an electrically conductive sealing plate 112 and 122, respectively, connected to the generator 20 that communicates electrosurgical energy through the tissue held therebetween.

Figure 2:
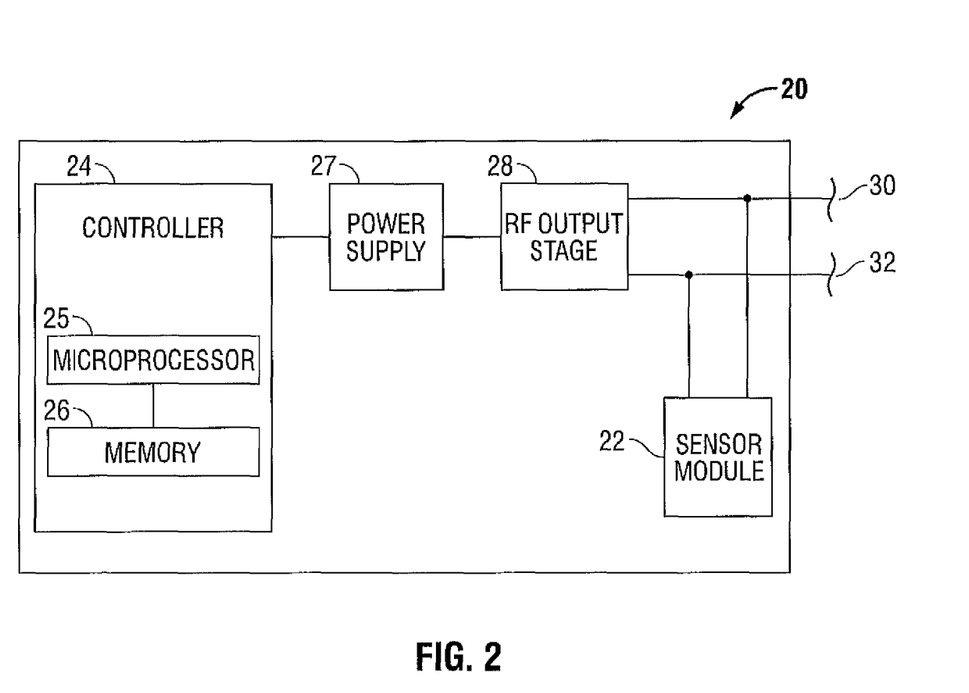
FIG. 2 is a schematic block diagram of a generator in accordance with one embodiment of the present disclosure.

Electrically conductive sealing plates 112 and 122, which act as active and return electrodes, are connected to the generator 20 through cable 23, which includes the supply and return lines coupled to the active and return terminals 30, 32 (FIG. 2). The cable 23 encloses the supply lines 4 and 8. The electrosurgical forceps 10 is coupled to the generator 20 at the active and return terminals 30 and 32 (e.g., pins) via a plug 92 disposed at the end of the cable 23, wherein the plug includes contacts from the supply and return lines. Electrosurgical RF energy is supplied to the forceps 10 by generator 20 via a supply line 4 connected to the active electrode and returned through a return line connected to the return electrode.

Forceps 10 generally includes a housing 60 and a handle assembly 74 that includes moveable handle 62 and handle 72, which is integral with the housing 60. Handle 62 is moveable relative to handle 72 to actuate the end effector assembly 40 to grasp and treat tissue. The forceps 10 also includes shaft 64 that has a distal end 68 that mechanically engages the end effector assembly 40 and a proximal end 69 that mechanically engages the housing 60 proximate a rotating assembly 80 disposed at a distal end of the housing 60.

With reference to FIG. 1, the generator 20 includes suitable input controls (e.g., buttons, activators, switches, touch screen, etc.) for controlling the generator 20. In addition, the generator 20 includes one or more display screens for providing the surgeon with variety of output information (e.g., intensity settings, treatment complete indicators, etc.). The controls allow the surgeon to adjust power of the RF energy, waveform, and other parameters to achieve the desired waveform suitable for a particular task (e.g., coagulating, tissue sealing, division with hemostasis, etc.). Further, the forceps 10 may include a plurality of input controls, which may be redundant with certain input controls of the generator 20. Placing the input controls at the forceps 10 allows for easier and faster modification of RF energy parameters during the surgical procedure without requiring interaction with the generator 20.

FIG. 2 shows a schematic block diagram of the generator 20 having a controller 24, a power supply 27, an RF output stage 28, and a sensor module 22. The power supply 27 may provide DC power to the RF output stage 28 that then converts the DC power into RF energy and delivers the RF energy to the forceps 10. The controller 24 includes a microprocessor 25 having a memory 26, which may be volatile type memory (e.g., RAM) and/or non-volatile type memory (e.g., flash media, disk media, etc.). The microprocessor 25 includes an output port connected to the power supply 27 and/or RF output stage 28, which allows the microprocessor 25 to control the output of the generator 20 according to either open and/or closed control loop schemes.

The generator 20 may include a plurality of connectors to accommodate various types of electrosurgical instruments (e.g., electrosurgical forceps 10, etc.). Further, the generator 20 may be configured to operate in a variety of modes such as ablation, monopolar and bipolar, cutting, coagulation, etc. It is envisioned that the generator 20 may also include a switching mechanism (e.g., relays) to switch the supply of RF energy between the connectors.

It is well known in the art that the resistance of the active and return lines 4 and 8 increases with the length of the lines 4 and 8. As the resistance increases, the maximum current that may be passed therethrough is limited accordingly. It may be desirable in certain electrosurgical procedures to provide relatively high current. This may be accomplished by increasing thickness of the wires, thereby reducing resistance of the active and return lines 4 and 8. However, this approach results in increased material use and is especially problematic when the electrosurgical instruments include relatively long wires, such as with endoscopic instruments.

The present disclosure provides for a system and method for supplying high voltage and low current power to the electrosurgical instrument and then stepping down the voltage and increasing the current accordingly. The stepped-down voltage and increase current power is then supplied by the transformer to one or more electrodes of the electrosurgical instrument.

Figure 3:
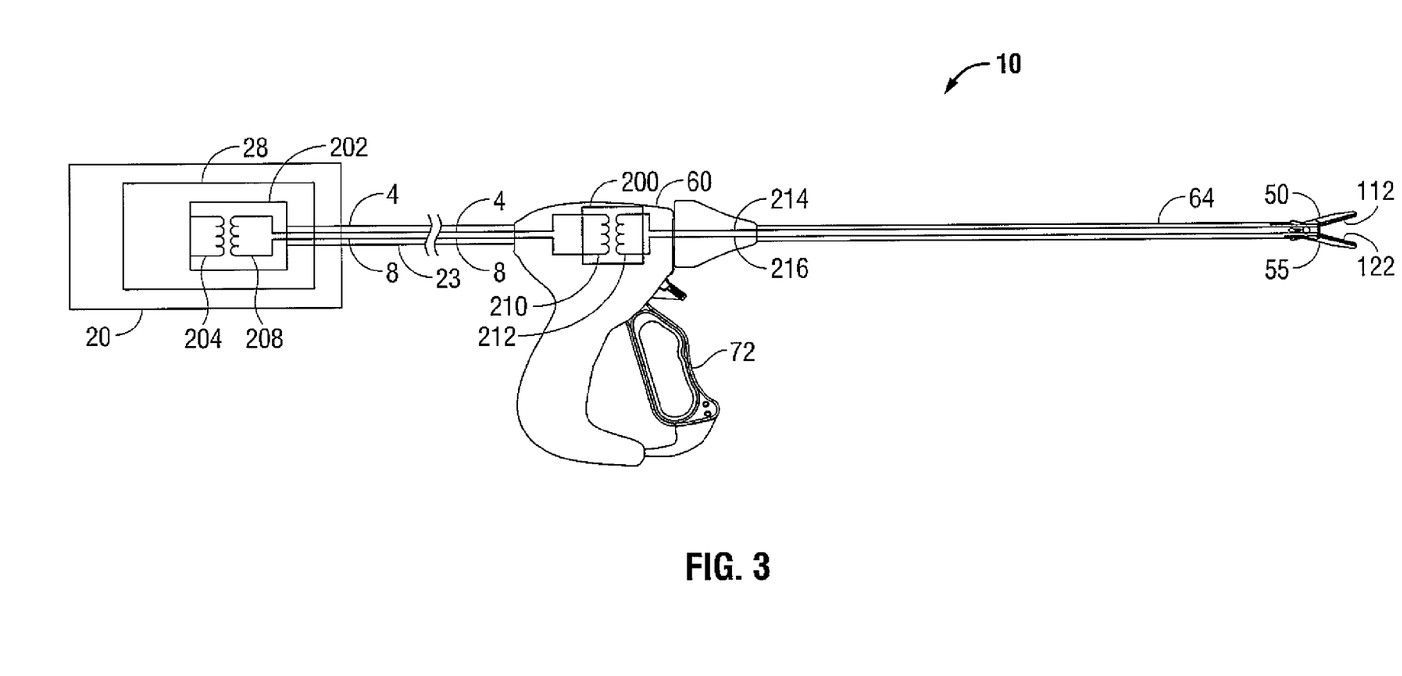
FIG. 3 is an electrical schematic diagram of an electrosurgical instrument according to one embodiment of the present disclosure.

FIG. 3 shows an electrical schematic diagram of the system 3 having a step down transformer 200 for stepping down the voltage and increasing current supplied by the generator 20. The step down transformer 200 may be adapted to operate with various other electrosurgical instruments. In addition, any other type voltage converters may be used in lieu of the step down transformer 200.

The RF output stage 28 may include an isolation transformer 202 that isolates the patient load from the high voltage power supply 27. The isolation transformer 202 includes a primary winding 204 and a secondary winding 208. The RF output stage 28 generates a radio frequency energy suitable for performing a particular electrosurgical procedure (e.g., coagulation, etc.) having a high voltage ($V_{HI}$) and low current that is then transformed by the isolation transformer 202. Various operational modes supply RF energy at various voltage and current levels. Those skilled in the art of transformer design may select any suitable step up ratio and line voltages.

The isolation transformer 202 includes a primary winding 204, which is electrically coupled to the power supply 27 and various components of the RF output stage 28. The transformer 202 also includes a secondary winding 208, which is connected to the forceps 10 through the cable 23. More specifically, each of the active and return lines 4 and 8 is electrically coupled to the secondary winding 208 of the transformer 202. As shown in FIGS. 1 and 3, the cable 23 connects the generator 20 to the forceps 10 allowing the electrosurgical energy to flow through the active and return lines 4 and 8 to the electrically conductive sealing plates 112 and 122.

The forceps 10 includes a step down transformer 200 that is disposed within the housing 60 or alternatively in the handle 72. In another embodiment, shown in FIG. 4, the transformer 200 is disposed at the distal end 68 of the shaft 64 in proximity to the jaw members 50 and 55. The transformer 200 includes a primary winding 210 and a secondary winding 212. The primary winding 210 is coupled to the active and return lines 4 and 8 and the secondary winding 212 is coupled to an active lead 214 and a return lead 216. The active and return leads 214 and 216 are disposed within the shaft 64 and are electrically coupled electrically conductive sealing plates 112 and 122 (e.g., active lead 214 is coupled to the sealing plate 112 and return lead 216 is coupled to the sealing plate 122).

Figure 4:
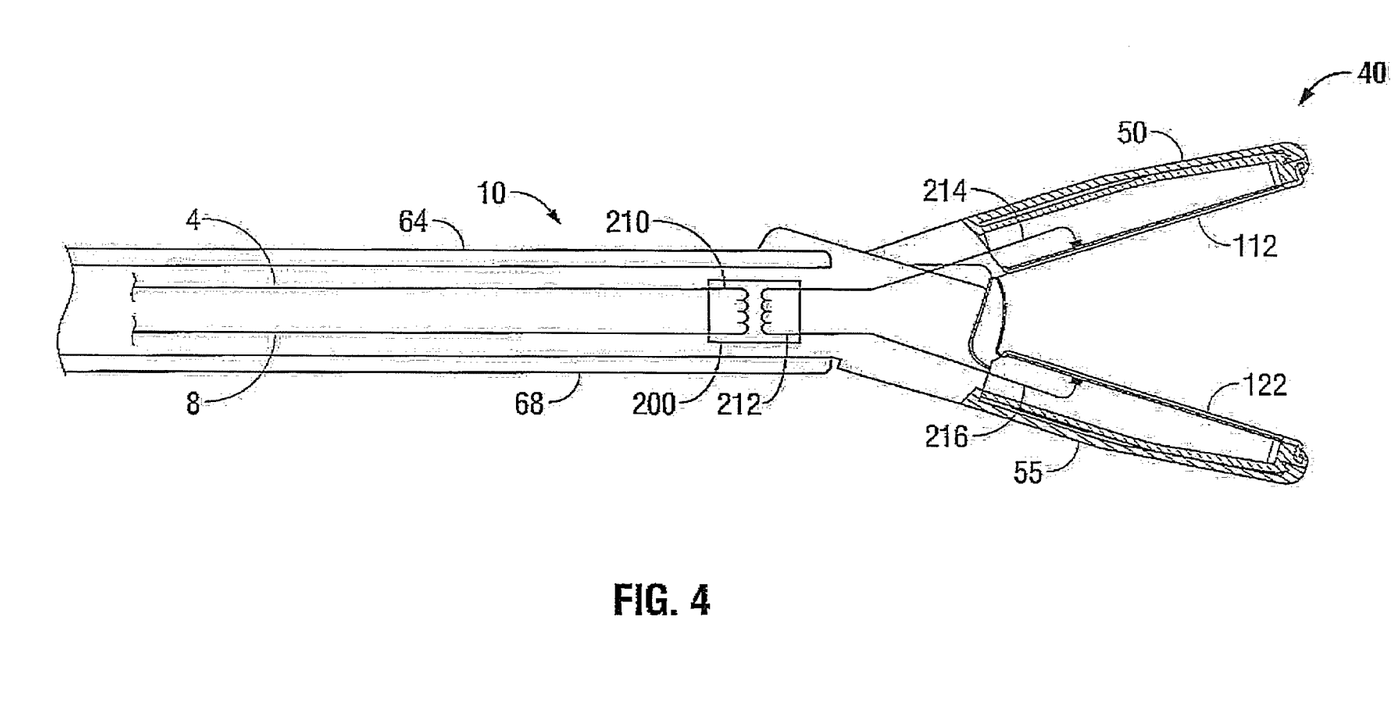
FIG. 4 is an electrical schematic diagram of an electrosurgical instrument according to another embodiment of the present disclosure.

The primary winding 210 includes a predetermined number of primary turns $N_P$ and the secondary winding 212 include a number of secondary turns $N_S$. The turns ratio between the primary and secondary turns ($N_P/N_S$) determines the step-down ratio of the transformer 210, which may be adjusted to achieve a desired step down voltage ($V_{DN}$). The energy supplied by the transformer 202 to the forceps may have high voltage and low current, allowing for current transmission along thinner conductors of the active and return lines 4 and 8 as well as through longer transmission distances (e.g., up to about 6 meters). Once the high voltage energy is transmitted to the forceps 10, the transformer 200 steps down the $V_{HI}$ to $V_{DN}$ thereby increasing the current of the transmitted energy. The stepped-down $V_{DN}$ is then transmitted along the active and return leads 214 and 216 to the electrically conductive sealing plates 112 and 122. The transformer 200 may have a predetermined step down ratio suitable for stepping down the high voltage power to lower voltage high current power. Any suitable ratio may be used to achieve a desired level of high current.

Figure 5:
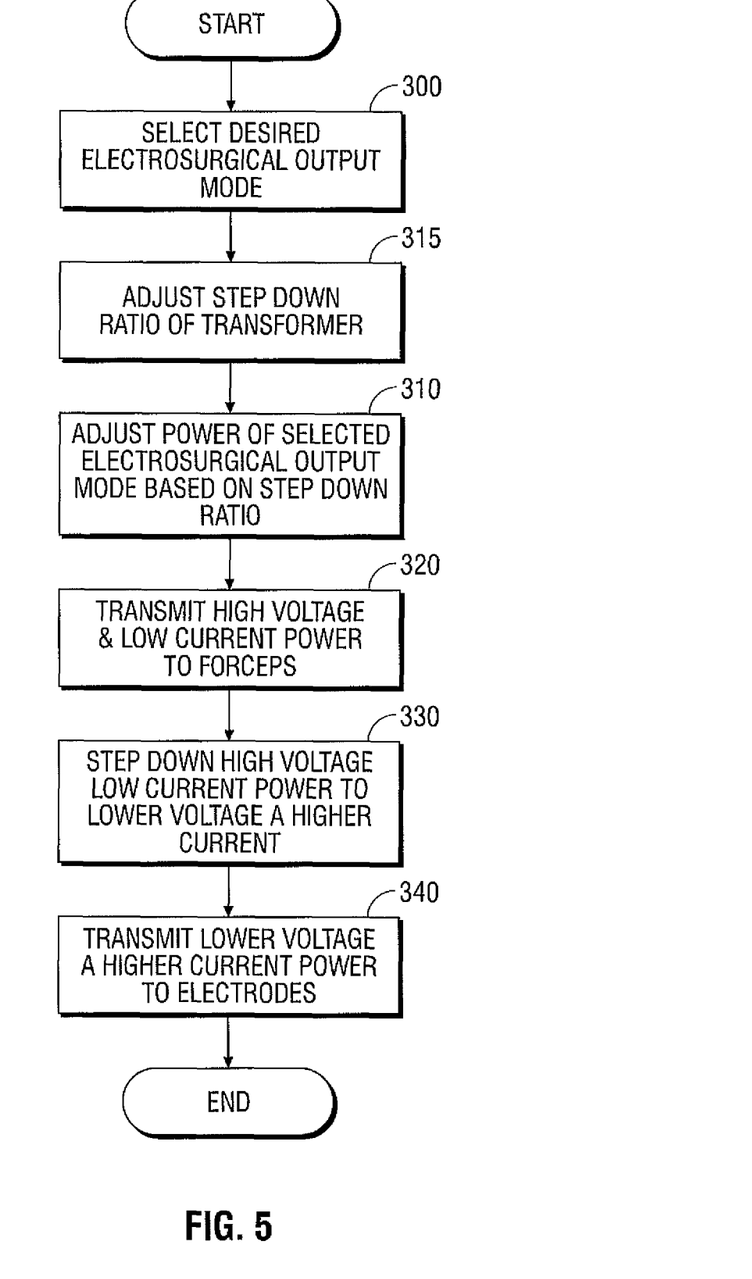
FIG. 5 is a flow chart of a method according to one embodiment of the present disclosure.

FIG. 5 shows a method for transmitting high voltage electrosurgical energy to the forceps 10 according to the present disclosure. In step 300, the generator 20 produces a desired electrosurgical energy output. This may be accomplished by selecting one of predetermined output modes (e.g., vessel sealing, bipolar coagulation, etc.) and/or setting intensity settings for the mode. The mode selection and user-adjustable settings set the voltage and current of the power to be supplied to the forceps 10.

After the selection of the desired mode is made, in step 310, the generator 20 adjusts the power of the selected energy output by compensating for the stepping, since the voltage of the actual output of the forceps 10 is going to be stepped-down at the forceps 10. The compensation may involve increasing the voltage and lowering the current, while taking into consideration the step down ratio of the transformer 200 or 250 of the forceps 10. The step down ratio may be preset manually, by the user of the generator 20 or automatically, by obtaining ratio data relating to the step down ratio of the transformer 200 from the forceps 10. In one embodiment, the forceps 10 may include an identifier adapted to be read by the generator 20. The identifier stores the ratio data that is then utilized by the generator 20 in adjusting the energy output to compensate for the stepping down at the forceps 10.

In step 315, the user may adjust the transformer 250 to achieve the desired step down ratio. In one embodiment, the generator 20 then may readjust the output power as discussed above with respect to step 310.

In step 320, the generator 20 transmits compensated high voltage and low current power to the forceps 10. In step 330, the forceps 10, and in particular the transformer 200 or 250 step down the energy from the generator 20 to lower voltage and higher current. In step 340, the stepped-down voltage is transmitted to the electrically conductive sealing plates 112 and 122.

The system and method according to the present disclosure provides for transmission of high voltage and low current power to the electrosurgical instruments. This allows for minimizing cable size, e.g., using less conductive material, thereby reducing material cost and waste. Conversely, this also allows for use of longer cables having thinner conductors, thereby minimizing the amount of material used.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical system, comprising:
an electrosurgical generator adapted to supply electrosurgical power, the electrosurgical generator including an isolation transformer; and
an electrosurgical device coupled to the electrosurgical generator, the electrosurgical device including:
a housing;
a shaft extending from the housing having an end-effector assembly disposed at a distal end thereof, the end effector assembly including opposing jaw members, at least one of the law members movable relative to the other from a first position wherein the jaw members are disposed in spaced relation relative to one another to at least a second position closer to one another wherein the jaw members cooperate to grasp tissue therebetween;
each jaw member including an electrically-conductive sealing plate, one of the electrically-conductive sealing plates functioning as an active electrode and the other electrically-conductive sealing plate functioning as a return electrode during activation such that electrosurgical energy flows from the active electrode through tissue positioned between the electrically-conductive sealing plates to the return electrode; and
a step-down transformer disposed at a distal end of the shaft in proximity to the jaw members, the step-down transformer including a primary winding coupled to the isolation transformer and a secondary winding coupled to an active lead of the active electrode and a return lead of the return electrode;
the active lead including a proximal end disposed within the distal end of the shaft:
the return lead including a proximal end disposed within the distal end of the shaft:
wherein the step-down transformer is adapted to step down the voltage of the electrosurgical power supplied by the electrosurgical generator.

2. The electrosurgical system according to claim 1, further comprising a cable adapted to interconnect the electrosurgical generator and the electrosurgical device, the cable including at least one active line and at least one return line.

3. The electrosurgical system according to claim 1, wherein the electrosurgical device is a bipolar device.

4. The electrosurgical system according to claim 3, wherein the bipolar device is an electrosurgical forceps.

5. An electrosurgical instrument configured to couple to an electrosurgical generator adapted to supply electrosurgical power to the electrosurgical instrument, the electrosurgical instrument comprising:
a housing;
a shaft extending from the housing having an end-effector assembly disposed at a distal end thereof, the end effector assembly including opposing jaw members, at least one of the jaw members movable relative to the other from a first position wherein the jaw members are disposed in spaced relation relative to one another to at least a second position closer to one another wherein the jaw members cooperate to grasp tissue therebetween;
each jaw member including an electrically-conductive sealing plate, one of the electrically-conductive sealing plates functioning as an active electrode and the other electrically-conductive sealing plate functioning as a return electrode during activation such that electrosurgical energy flows from the active electrode through tissue positioned between the electrically-conductive sealing plates to the return electrode; and
a step-down transformer disposed at a distal end of the shaft in proximity to the jaw members, the step-down transformer including a primary winding configured to couple to an isolation transformer and a secondary winding coupled to an active lead of the active electrode and a return lead of the return electrode;
the active lead including a proximal end disposed within the distal end of the shaft:
the return lead including a proximal end disposed within the distal end of the shaft:
wherein the step-down transformer is adapted to step down the voltage of the electrosurgical power supplied to the electrosurgical instrument.

6. The electrosurgical instrument according to claim 5, wherein the electrosurgical instrument is an electrosurgical forceps.

* * * * *